US008866052B2

(12) United States Patent
Nhan et al.

(10) Patent No.: US 8,866,052 B2
(45) Date of Patent: Oct. 21, 2014

(54) HEATING ARTICLES USING CONDUCTIVE WEBS

(75) Inventors: Davis-Dang Hoang Nhan, Appleton, WI (US); Sudhanshu Gakhar, Neenah, WI (US); Thomas Michael Ales, III, Neenah, WI (US); Sridhar Ranganathan, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1535 days.

(21) Appl. No.: 12/473,763

(22) Filed: May 28, 2009

(65) Prior Publication Data

US 2009/0294435 A1 Dec. 3, 2009

Related U.S. Application Data

(60) Provisional application No. 61/130,220, filed on May 29, 2008.

(51) Int. Cl.

| | |
|---|---|
| ***H05B 3/10*** | (2006.01) |
| ***D04H 1/42*** | (2012.01) |
| ***D04H 1/4374*** | (2012.01) |
| ***H05B 3/34*** | (2006.01) |
| ***H01B 1/24*** | (2006.01) |
| ***D04H 1/4242*** | (2012.01) |
| *A61F 13/00* | (2006.01) |

(52) U.S. Cl.

CPC .......... *H05B 3/347* (2013.01); *H05B 2203/017* (2013.01); *D04H 1/42* (2013.01); *D04H 1/4374* (2013.01); *H05B 2203/026* (2013.01); *H05B 2203/036* (2013.01); *H01B 1/24* (2013.01); *D04H 1/4242* (2013.01)

USPC .............. 219/553; 219/544; 219/545; 602/41

(58) Field of Classification Search

USPC ..................... 219/528-9, 545, 548-9, 552-3; 602/41-2; 604/73, 289, 290, 304-5, 604/310, 543

See application file for complete search history.

(56) References Cited

U.S. PATENT DOCUMENTS

| | | | |
|---|---|---|---|
| 3,148,107 | A | 9/1964 | Selke et al. |
| 3,265,557 | A | 8/1966 | De Fries et al. |
| 3,367,851 | A | 2/1968 | Filreis et al. |
| 3,539,296 | A | 11/1970 | Selke |
| 3,774,299 | A | 11/1973 | Sato et al. |
| 3,859,504 | A | 1/1975 | Motokawa et al. |

(Continued)

FOREIGN PATENT DOCUMENTS

| | | | |
|---|---|---|---|
| EP | 0 563 919 | A1 | 10/1993 |
| EP | 1 118 085 | B1 | 7/2006 |
| WO | WO 2006/054853 | A1 | 5/2006 |

*Primary Examiner* — Shawntina Fuqua

(74) *Attorney, Agent, or Firm* — Denise L. Stoker; Randall W. Fieldhack

(57) ABSTRACT

A heating article is provided including a heating element including a first layer of nonwoven fibers mixed with conductive fibers, wherein the layer is divided to include a conductive region and a nonconductive region, wherein the conductive region extends in a co-extensive and co-planar pattern in a majority of the layer, and wherein the conductive region has first and second ends, and a power source removably coupled to the first and second ends. The first layer can include nonwoven fibers mixed with non-metallic conductive fibers. The heating article can also include a second layer superposed with the first layer, wherein the second layer is substantially free of non-metallic conductive fibers.

20 Claims, 2 Drawing Sheets

(56) References Cited

U.S. PATENT DOCUMENTS

| | | | | |
|---|---|---|---|---|
| 3,998,689 | A | 12/1976 | Kitago et al. | |
| 4,032,607 | A | 6/1977 | Schulz | |
| 4,115,917 | A | 9/1978 | Charon et al. | |
| 4,250,397 | A | 2/1981 | Gray et al. | |
| 4,256,801 | A | 3/1981 | Chuluda | |
| 4,347,104 | A | 8/1982 | Dressler | |
| 4,523,086 | A | 6/1985 | Eilentropp | |
| 4,534,886 | A | 8/1985 | Kraus et al. | |
| 4,606,790 | A | 8/1986 | Youngs et al. | |
| 4,728,395 | A | 3/1988 | Boyd, Jr. | |
| 4,909,901 | A | 3/1990 | McAllister et al. | |
| 4,960,979 | A | 10/1990 | Nishimura | |
| 5,206,466 | A | 4/1993 | Inamiya | |
| 5,582,757 | A | 12/1996 | Kio et al. | |
| 6,452,138 | B1 | 9/2002 | Kochman et al. | |
| 6,540,874 | B1 | 4/2003 | Ling Chen | |
| 6,593,555 | B2 | 7/2003 | Hayashi | |
| 7,238,196 | B2 * | 7/2007 | Wibaux | 607/96 |
| 8,283,602 | B2 * | 10/2012 | Augustine et al. | 219/212 |
| 2003/0155347 | A1 | 8/2003 | Oh et al. | |
| 2005/0051536 | A1 | 3/2005 | Shirlin et al. | |
| 2005/0134162 | A1 | 6/2005 | Hiraki | |
| 2006/0096115 | A1 | 5/2006 | Lee | |
| 2006/0278631 | A1 | 12/2006 | Lee et al. | |
| 2008/0064997 | A1 * | 3/2008 | Flick | 602/42 |
| 2009/0036850 | A1 | 2/2009 | Nhan et al. | |
| 2009/0295657 | A1 | 12/2009 | Gakhar et al. | |

* cited by examiner

HEATING ARTICLES USING CONDUCTIVE WEBS

This application claims priority to provisional application Ser. No. 61/130,220 entitled Products Using Conductive Webs and filed in the U.S. Patent and Trademark Office on May 29, 2008. The entirety of provisional application Ser. No. 60/130,220 is hereby incorporated by reference.

BACKGROUND

A need exists for heating elements for use in various products in which the heating elements and/or products themselves can benefit from being made fully or partially disposable for reasons including saving on manufacturing costs and avoiding transmitting substances from one user to another.

This disclosure describes the use of a conductive paper (cellulose and carbon fiber composite) in heating/warming applications. Significant work has been performed to explore the heating characteristics and efficiency of conductive paper as a heating material. Commercial development of conductive paper for other applications has shown the potential high efficiency and low cost this material can bring to heating/warming arenas.

SUMMARY

The present disclosure is generally directed to a conductive nonwoven web that may be used in numerous heating applications. The disclosure described herein solves the problems described above and provides an increase in efficacy in various heating products.

More specifically, the present disclosure provides a heating article including a heating element including a first layer of nonwoven fibers mixed with conductive fibers, wherein the layer is divided to include a conductive region and a nonconductive region, wherein the conductive region extends in a co-extensive and co-planar pattern in a majority of the layer, and wherein the conductive region has first and second ends, and a power source removably coupled to the first and second ends.

The present disclosure also provides a heating article including a heating element including a first layer of nonwoven fibers mixed with non-metallic conductive fibers, wherein the layer is divided to include a conductive region and a nonconductive region, wherein the conductive region extends in a co-extensive and co-planar pattern in a majority of the layer, and wherein the conductive region has first and second ends, and a second layer superposed with the first layer, wherein the second layer is substantially free of non-metallic conductive fibers. The heating article also includes a power source removably coupled to the first and second ends.

Other features and aspects of the present disclosure are discussed in greater detail below.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings, where:

Figure 1:
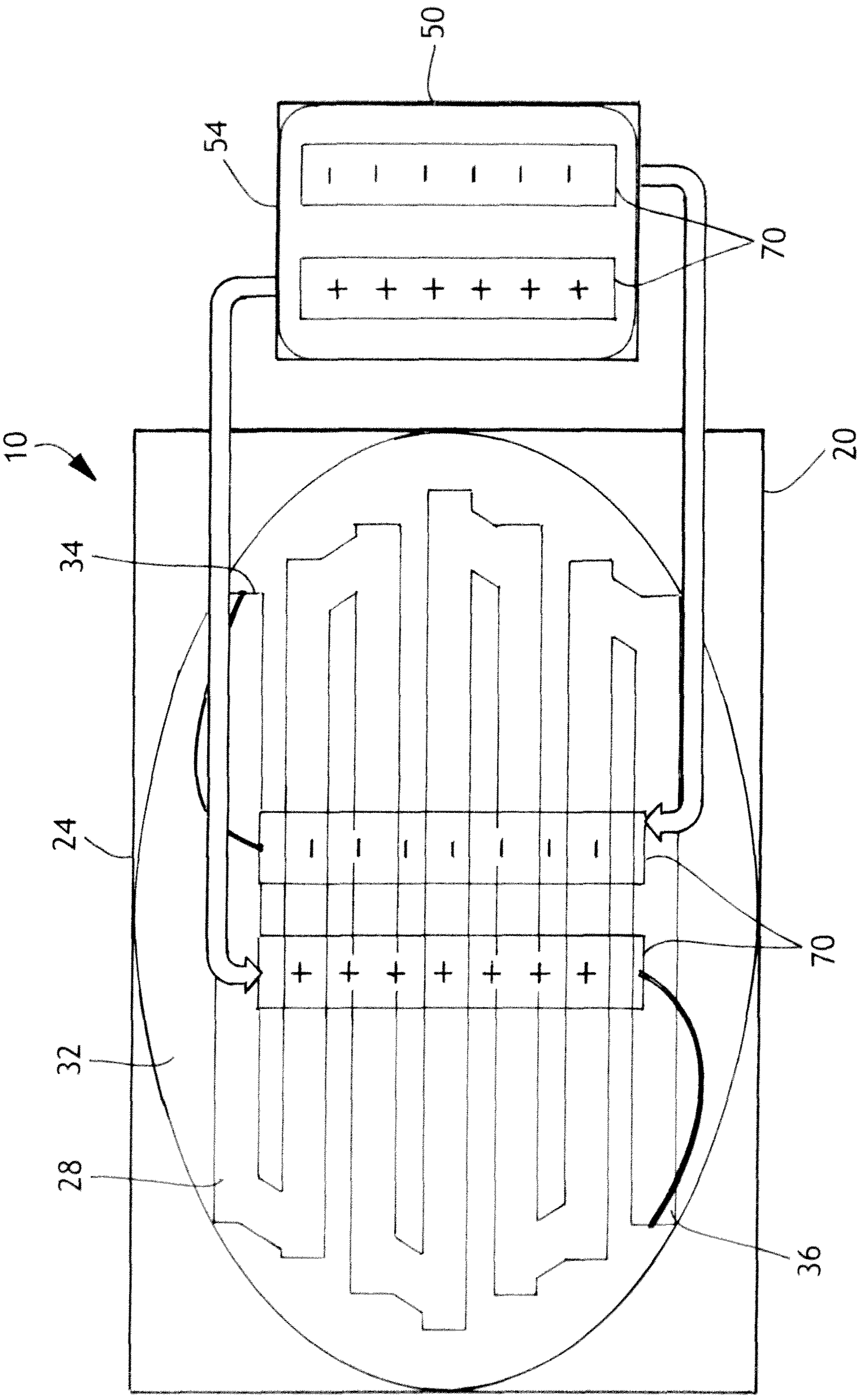
FIG. 1 is a plan schematic view of a heating article of the present application.

Repeat use of reference characters in the present specification and drawings is intended to represent the same or analogous features or elements of the present disclosure. The drawings are representational and are not necessarily drawn to scale. Certain proportions thereof may be exaggerated, while others may be minimized.

DETAILED DESCRIPTION

It is to be understood by one of ordinary skill in the art that the present discussion is a description of exemplary aspects of the present disclosure only, and is not intended as limiting the broader aspects of the present disclosure.

The present disclosure is generally directed to heating products including a conductive element. Some products described herein are disposable, meaning that they are designed to be discarded after a limited use rather than being laundered or otherwise restored for reuse.

Conductive webs and conductive web manufacturing processes are described in more detail in co-pending and co-owned U.S. patent applications Ser. Nos. 12/130,573 and 12/341,419, the disclosures of which are incorporated herein by reference to the extent that they are non-contradictory herewith.

The conductive fibers that may be used in accordance with the present disclosure can vary depending upon the particular application and the desired result. Conductive fibers that may be used to form the nonwoven webs include carbon fibers, metallic fibers, conductive polymeric fibers including fibers made from conductive polymers or polymeric fibers containing a conductive material, and mixtures thereof. Metallic fibers that may be used include, for instance, copper fibers, aluminum fibers, and the like. Polymeric fibers containing a conductive material include thermoplastic fibers coated with a conductive material or thermoplastic fibers impregnated or blended with a conductive material. For instance, in one aspect, thermoplastic fibers that are coated with silver may be used.

Carbon fibers that may be used in the present disclosure include fibers made entirely from carbon or fibers containing carbon in amounts sufficient so that the fibers are electrically conductive. In one aspect, for instance, carbon fibers may be used that are formed from a polyacrylonitrile polymer. In particular, the carbon fibers are formed by heating, oxidizing, and carbonizing polyacrylonitrile polymer fibers. Such fibers typically have high purity and contain relatively high molecular weight molecules. For instance, the fibers can contain carbon in an amount greater than about 90% by weight, such as in an amount greater than 93% by weight, such as in an amount greater than about 95% by weight. Polyacrylonitrile-based carbon fibers are available from numerous commercial sources including from Toho Tenax America, Inc., Rockwood, Tenn.

Other raw materials used to make carbon fibers are rayon and petroleum pitch.

In forming conductive nonwoven webs in accordance with the present disclosure, the above conductive fibers are combined with other fibers suitable for use in tissue making processes. The fibers combined with the conductive fibers may include any natural or synthetic cellulosic fibers including, but not limited to, nonwoody fibers, such as cotton, abaca, kenaf, sabai grass, flax, esparto grass, straw, jute hemp, bagasse, milkweed floss fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898, issued Dec. 27, 1988 to Laamanen et al.; U.S. Pat. No. 4,594,130, issued Jun. 10, 1986 to Chang et al.; and U.S. Pat. No. 3,585,104 issued Jun. 15, 1971 to Kleinert. Useful fibers can also be produced by anthraquinone pulping, exemplified by U.S. Pat. No. 5,595,628 issued Jan. 21, 1997, to Gordon et al.

A portion of the fibers, such as up to 100% or less by dry weight, can be synthetic fibers such as rayon, polyolefin fibers, polyester fibers, polyvinyl alcohol fibers, bicomponent sheath-core fibers, multi-component binder fibers, and the like. An exemplary polyethylene fiber is Pulpex®, available from Hercules, Inc. located at Wilmington, Del. U.S.A. Synthetic cellulose fiber types include rayon in all its varieties and other fibers derived from viscose or chemically-modified cellulose.

In general, the products of the present disclosure can be used in conjunction with any known materials and chemicals that are not antagonistic to its intended use. Examples of such materials include but are not limited to baby powder, baking soda, chelating agents, zeolites, perfumes or other odor-masking agents, cyclodextrin compounds, oxidizers, and the like. Of particular advantage, when carbon fibers are used as the conductive fibers, the carbon fibers also serve as odor absorbents. Superabsorbent particles, synthetic fibers, or films may also be employed. Additional options include dyes, optical brighteners, humectants, emollients, and the like.

Nonwoven webs made in accordance with the present disclosure can include a single homogeneous layer of fibers or may include a stratified or layered construction. For instance, the nonwoven web ply may include two or three layers of fibers. Each layer may have a different fiber composition. Each of the fiber layers can include a dilute aqueous suspension of fibers. The type of particular fibers contained in each layer generally depends upon the product being formed and the desired results. In one aspect, for instance, a middle layer contains pulp fibers in combination with the conductive fibers. Outer layers, on the other hand, can contain only pulp fibers, such as softwood fibers and/or hardwood fibers.

Placing the conductive fibers within the middle layer may provide various advantages and benefits. Placing the conductive fibers in the center of the web, for instance, can produce a conductive material that still has a soft feel on its surfaces. Concentrating the fibers in one of the layers of the web can also improve the conductivity of the material without having to add great amounts of the conductive fibers. In one aspect, for instance, a three-layered web is formed in which each layer accounts for from about 15% to about 40% by weight of the web. The outer layers can be made of only pulp fibers or a combination of pulp fibers and thermoplastic fibers. The middle layer, on the other hand, may contain pulp fibers combined with conductive fibers. The conductive fibers may be contained in the middle layer in an amount from about 30% to about 70% by weight, such as in an amount from about 40% to about 60% by weight, such as in an amount from about 45% to about 55% by weight.

The conductivity of the nonwoven web can also vary depending upon the type of conductive fibers incorporated into the web, the amount of conductive fibers incorporated into the web, and the manner in which the conductive fibers are positioned, concentrated or oriented in the web. In one aspect, for instance, the nonwoven web can have a resistance of less than about 1500 Ohms/square, such as less than about 100 Ohms/square, such as less than about 10 Ohms/square.

The conductivity of the sheet is calculated as the quotient of the resistance measurement of a sheet, expressed in Ohms, divided by the ratio of the length to the width of the sheet. The resulting resistance of the sheet is expressed in Ohms per square. More specifically, the resistance measurement is in accordance with ASTM F1896-98 "Test Method for Determining the Electrical Resistivity of a Printed Conductive Material". The resistance measuring device (or Ohm meter) used for carrying out ASTM F1896-98 is a Fluke multimeter (model 189) equipped with Fluke alligator clips (model AC120); both are available from Fluke Corporation, located at Everett, Wash. U.S.A.

One example of a conductive web of the present disclosure includes the following. The conductive web is manufactured by co-forming chopped carbon fibers with cellulose or synthetic material. The carbon fiber has a fiber width of 0.0002-0.0004 inches (5-10 μm) in diameter, a fiber length of 3 mm chopped, consists mostly of carbon atoms with a purity of 92-95%, and includes water-soluble sizing. The conductive web typically includes 10% carbon fiber and 90% cellulosic pulp blend. Additives for wet strength and coloration can be included. Layering capability can be used to focus carbon fiber in a middle layer of a three-layer tissue sheet having low basis weight and strength, but more stretch. For conductive paper, a monolayer flat paper is formed that is traditionally uncreped. The conductive paper has a higher basis weight and strength, but can be brittle. The cellulose to synthetic fiber ratio can be adjusted to vary material properties. Alternately, the conductive web can be formed from a meltblown web with carbon fiber in a coform process.

The resulting conductive web made in accordance with the present disclosure may be used alone as a single ply product or can be combined with other webs to form a multi-ply product. In one aspect, the conductive nonwoven web may be combined with other tissue webs to form a 2-ply product or a 3-ply product. The other tissue webs, for instance, may be made entirely from pulp fibers and can be made according to any of the processes described above.

In an alternative aspect, the conductive nonwoven web made according to the present disclosure may be laminated using an adhesive or otherwise to other nonwoven or polymeric film materials. For instance, in one aspect, the conductive nonwoven web may be laminated to a meltblown web and/or a spunbond web that are made from polymeric fibers, such as polypropylene, polyester, or bicomponent fibers. As described above, in one aspect, the conductive nonwoven web can contain synthetic fibers. In this aspect, the nonwoven web may be bonded to an opposing web containing synthetic fibers such as a meltblown web or spunbond web.

Incorporating the conductive nonwoven web into a multi-ply product may provide various advantages and benefits. For instance, the resulting multi-ply product may have better strength, may be softer, and/or may have better liquid wicking properties.

In one aspect, the conductive fibers may be contained within the nonwoven web so as to form distinct zones of conductivity. For instance, in one aspect, a head box may be used instead of or in addition to separating the fibers through the thickness of the web. The head box may be designed to also separate the fibers in the plane of the web. In this manner, conductive fibers may only be contained in certain zones along the length (machine direction) of the web. The conductive zones may be separated by non-conductive zones that only contain non-conductive materials such as pulp fibers.

Figure 2:
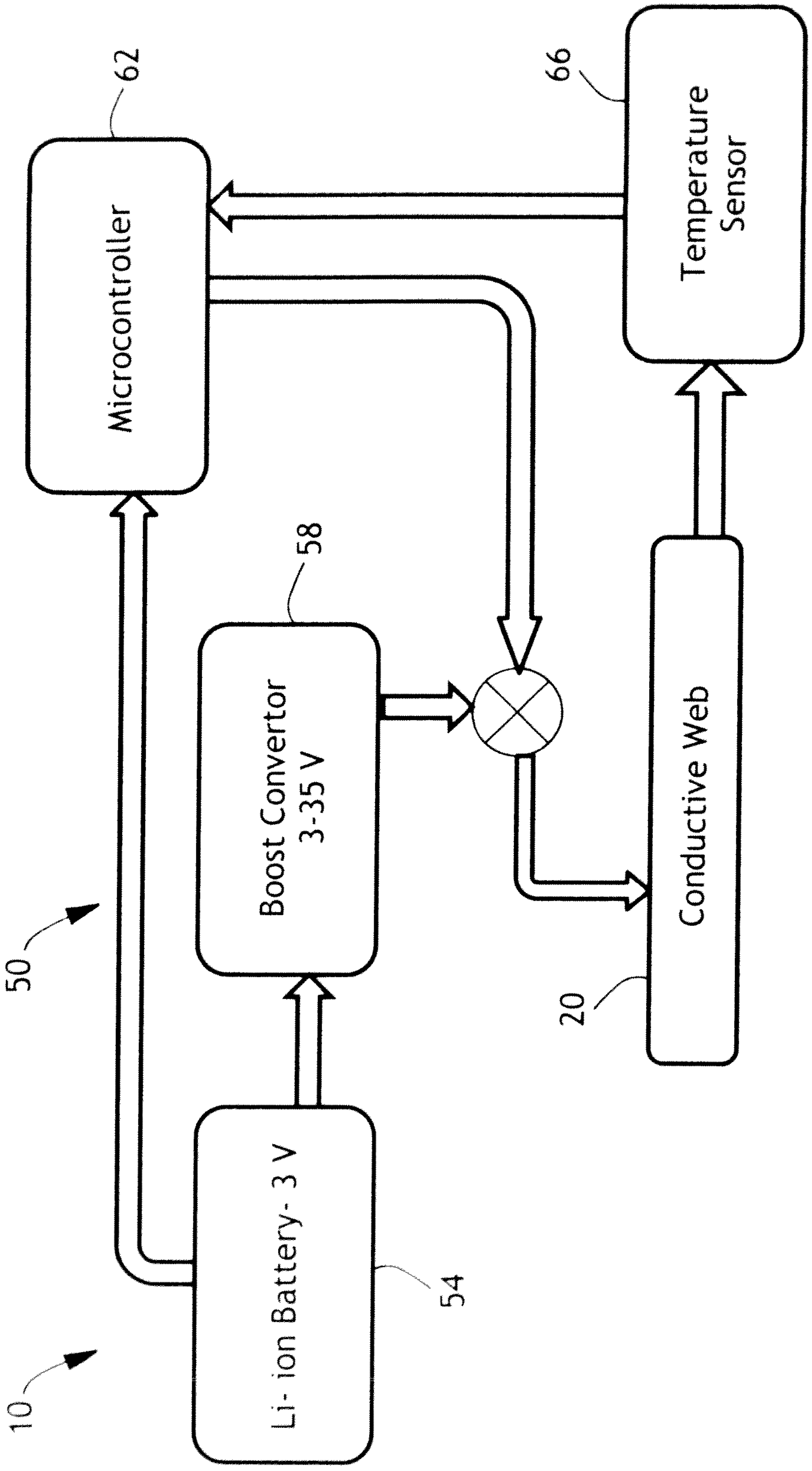
FIG. 2 is a schematic of a power and control circuit to be used in conjunction with the heating article of FIG. 1.

For exemplary purposes and as illustrated in FIGS. 1 and 2, a product made in accordance with the disclosed technology can be a heating article 10 made for use as a portable device for therapeutic heating and other low cost heating applications. Heat therapy reduces pain, especially the pain of muscle tension or spasm. Further, patients with other types of pain can benefit. Heat therapy acts to: (1) Increase the blood flow to the skin. (2) Dilate blood vessels, increasing oxygen and nutrient delivery to local tissues. (3) Decrease joint stiffness by increasing muscle elasticity. The portable heating article 10 can generally include a disposable heating element 20, a power source 50 such as a reusable battery-operated control unit, and a mechanical and/or electrical means to connect the disposable heating element 20 to the power source 50.

The heating article 10 includes a disposable heating element 20 incorporating a first layer 24 formed from nonwoven fibers mixed with non-metallic conductive fibers as described above. The first layer 24 is divided to include a conductive region 28 and a non-conductive region 32. In one aspect of the present disclosure, the conductive region 28 extends in a co-extensive and co-planar pattern in a majority of the first layer 24. The conductive region 28 includes first and second ends or leads 34, 36 to which the power source 50 can be connected.

FIG. 1 illustrates one aspect of the present disclosure in more detail. With respect to the heating element 20, heat can be provided by a winding coil of the conductive region 28 as shown in FIG. 1. The reason for the coil design is to focus and disperse the heating action throughout the heating element 20.

The conductive and non-conductive regions 28, 32 of the first layer 24 can be formed through conductive fiber zoning as described above. In an alternative aspect of the present disclosure, the conductive and non-conductive regions 28, 32 of the first layer 24 can be formed using bonding. Bond lines can be formed into the nonwoven web to form different zones of conduction. Further information with respect to circuits formed through bonding and other means is available in co-pending and co-owned U.S. patent application Ser. No. 8,172,982, the disclosure of which is incorporated herein by reference to the extent that it is non-contradictory herewith.

For creation of a circuit from the conductive web, it is essential to break, remove or alter some of the carbon-to-carbon fiber bonds and create areas of higher resistance in the conductive web. This can be accomplished by ultrasonic or pressure bonds applied to the web during processing. The bonding techniques are well known in the industry and can be configured in a multitude of patterns to create specific avenues of greater or lesser resistance that define a circuit. For example, ultrasonic bonding technology imparts enough energy into the web to break the brittle conductive fiber material but leave the substrate behind. Circuit paths can be processed at high speeds and efficiencies making it possible to produce low cost disposable circuits in a variety of health and hygiene products or other consumer products. The width of the bond as well as the pressure or intensity of the bond when applied can determine the extent of the resistance increase. Areas that are not affected by the bonding process are left at the same conductive level. This type of processing can easily be adapted for current industry use to create high throughput tissue circuits.

Other methods to create circuit paths include mechanical methods such as flex knife and die cutting the conductive tissue or material to sever or remove the conductive tissue in areas in which high resistance is required. This is essentially cutting out a circuit pattern using standard process technologies. The mechanical cutting, pressure bonding, and ultrasonic bonding techniques can all be used together to most efficiently produce the circuit pattern and can be done using rotary or plunge mechanical technologies.

The resistance of the heating element 20 can be tuned for customized applications. In one aspect, increasing the percentage of conductive fibers in the heating element 20 reduces the resistance of the heating element 20, thus providing less heating. In another aspect, the heating element 20 can be layered with the first and second ends 34, 36 of one layer electrically connected to the first and second ends of another layer, similar to resistors connected in parallel. Each layer has an inherent resistance. When combining the resistors in parallel, the reciprocal values of the resistances are effectively added as is well known. The ends can be electrically connected using bonds, conductive pins or adhesives, or by any other suitable method, thereby creating an electrically conductive bond between the layers.

In another aspect of the present disclosure, polymeric fibers can make up some or all of the nonwoven fibers. In addition, any suitable fibers, whether cellulosic or polymeric, and appropriate surface treatments, can be chosen such that the first layer is absorbent. The selection of conductive and non-conductive materials can be tailored such that the first layer is inexpensive enough to be disposable, yet be durable enough for its intended use.

Alternately, the thermal conductivity of the heating element 20 can be customized. Polymer fibers act as a thermal insulator so the variation of polymer fibers can tune the thermal conductivity of the heating element 20. Layering polymer fibers can also focus the directivity of heating. An extra layer of synthetic or natural fibers can be used to provide insulation to minimize heat loss to the environment. An aluminum vapor-deposited film, described in more detail below, can also be used to reflect heat to the body of a user.

The heating article 10 can be scaled to meet various requirements, including scaled to produce heating within ranges that are therapeutic for humans. The resistivity of the conductive region 28 can be altered by varying the concentration of conductive fibers and by varying the width and thickness of the conductive region 28. In addition, the power source 50 can be scaled such that heat is generated in therapeutic ranges. At the same time, the resistivity of the conductive region 28 and power provided by the power source 50 are selected to avoid excessive power requirements. One key therapeutic heating temperature is approximately 97 degrees Fahrenheit, although that temperature will vary by individual and by application, as is known in the art. In addition, it is desirable that the power source 50 last for the intended therapeutic time. For example, an eight-hour battery life is often sufficient to accommodate a therapeutic heating session. Also, a rechargeable battery is desirable, particularly for sustainability reasons. The battery ideally is rechargeable due to the high current draw required to power the heating element. A basic review of power equations dictates the current, voltage, and resistance requirements to optimize the functionality of the heating element. For example, a temperature of 97 degrees Fahrenheit for a therapeutic heating article 10 can be achieved with a 39 gsm conductive paper having a conductive fiber concentration of 12 percent connected to a power source of 6.7 V and 205 mA along the length of the article (5 cm×6.8 cm).

More specifically, either a disposable battery or a rechargeable battery can be used to facilitate portability of the heating article 10. In one potential aspect illustrated in FIG. 2, a 3V lithium ion rechargeable battery 54 is used. Other battery technologies such as Li-polymer or Zn-air can also be used.

The battery 54 also needs to be of sufficient size to provide sufficient current. The voltage output of the battery 54 in the power source 50 is boosted with an integrated circuit to the applicable potential. For example, the battery 54 can be connected to a boost converter 58 such as the MAX669 controller available from Maxim Integrated Products. The boost converter 58 converts the 3V from the battery to 24V. The battery 54 is also used to power a microcontroller 62 such as the PIC 16F876A microcontroller available from Microchip Technology Inc. The microcontroller 62 uses a temperature sensor 66 to monitor the temperature of the heating element 20 and to control it to the desired temperature using a pulse width modulation (PWM) signal. The PWM signal generated by the microcontroller 62 is mixed with the boost voltage to heat the heating element 20.

In addition, the circuit shown in FIG. 2 can be used to control the heating element 20. In common chemical heaters, opening the package causes the heater to become activated due to contact with air, and the heating generally takes several minutes. The chemical heater generally provides heat until the chemical reaction is depleted, and the amount of heat typically drops slowly over use. In the present disclosure with electronic control, the heating element 20 can provide constant heat output, the heating element 20 can be cycled to have a heat pulse, the heat can rise slowly to peak then drop over time, or any other suitable control scheme can be used. In addition, the heating element 20 of the present disclosure heats to a reasonable temperature for therapeutic applications very quickly, typically within seconds.

In another aspect of the present disclosure, the power source 50 can be plugged into a wall outlet or other power supply, and can include a transformer and other circuitry needed to supply the appropriate power to the heating element 20.

Internal to the heating element 20, the conductive region 28 can be a winding coil of the conductive web that attaches to the power source 50 at the two terminals or ends 34, 36 shown in FIG. 1. The two ends 34, 36 can be in any suitable configuration as long as they accommodate connection to the power source 50.

In one aspect of the present disclosure, the power source 50 is removably coupled to the first and second ends 34, 36 by any suitable means. Suitable means include standard or custom-designed connectors, metallic clamps or alligator clips, snaps, buttons, conductive hook-and-loop material, along with any other suitable means including the types described in co-pending and co-owned U.S. patent application Ser. No. 11/740,671, the disclosure of which is incorporated herein by reference to the extent that it is non-contradictory herewith. An ideal application of the battery 54 has a minimum of expensive small connectors that can require more handling during manufacturing. In one aspect of the present disclosure, cost can be reduced by using a rechargeable battery pack that is wrapped in a conductive hook or loop material, where the heating element 20 includes the opposite loop material. The larger surface area of the conductive hook and loop ensures a lower connection resistance for the power supply 50 to the heating element 20.

In another aspect of the present disclosure, the first and second ends 34, 36 can be coupled to the power source 50 by printing a conductive trace adjacent to each end. In one aspect, a good electrical connection can be achieved by screen printing a conductive tissue with a silver ink trace at each end, and using a metal clip connected to a power source 50. Silver ink has been found to penetrate deep inside the structure of conductive paper. In other aspects, any suitable conductive material and printing process can be used.

In various aspects of the present disclosure, the power source 50 is durable and reusable. In other words, the power source 50 is removable from the disposable heating element 20 and reusable with another heating element 20.

To facilitate coupling of the power supply 50 to the heating element 20, one or both of the heating element 20 and the power supply 50 can be labeled 70 so that a user can properly orient the two when coupling them. The area in which the power source 50 is coupled to the heating element 20 can be labeled to match the power source 50 for correct placement. Although in this application there is generally no incorrect way to couple the power source 50 the heating element 20, such labeling 70 serves to reassure the consumer.

In an alternate aspect of the present disclosure, the power source 50 or the heating element 20 can include an electronic temperature control of any suitable type that is sufficient to maintain the temperature of the heating element within an intended range.

In another aspect of the present disclosure, the heating element 20 can include one or more additional layers, each of similar or complementary design to the first layer 24. Each additional layer is superposed with the first layer 24 and can include nonwoven fibers mixed with non-metallic conductive fibers, wherein each additional layer is also divided to include a conductive region 28 and a non-conductive region 32. The heating element 20 can be constructed from several layers of conductive paper to build a heating element 20 with lower overall resistance and higher thermal mass. Each heating layer can be separated by another layer that is either electrically or thermally insulating (or both) as appropriate. The layers can also be placed immediately in a face-to-face orientation with the next layer without an interposed insulating layer. Because each layer has an inherent facing substantially free of conductive fibers, the layers can be stacked without an insulating separator.

In still other aspects of the present disclosure, the heating element 20 can also include one or more fluid-resistant layers made from a polymeric film, such as polyethylene film, or other suitable material to protect the conductive regions 28 from electrical shorting due to the presence of water or other conductive fluid. In addition, the heating element 20 can include one or more absorbent layers of suitable construction superposed with the other layers. Such an absorbent layer can be separated from the conductive regions 28 by a fluid-resistant layer. Further, the heating element 20 can include one or more protective layers of polymeric film or other suitable material intended to protect the conductive regions 28 from performance-limiting damage. In addition, the heating element 20 can include a pressure sensitive adhesive layer on the body side of the heating element 20 to facilitate removable attachment of the heating element 20 to the body of a user. The adhesive layer can cover all or only a portion, such as the perimeter, of the heating element 20. Finally, the heating element 20 can also include one or more full or partial heat-reflective layers such as aluminum vapor deposited film, to help focus the heating from the heating element 20 in a particular direction.

For heating applications, the heating article 10 can be used as a therapeutic heater in either disposable or durable versions (e.g., muscle soreness, patient warming). Additional heating applications include floor mats, flooring substrate for infrastructure heating, and hanging space heaters. The heating properties can also be used in combination with thermochromic inks for inexpensive displays that respond to different temperatures by displaying different images on one substrate. More specifically, the heating article 10 of the present disclosure can be used for therapeutic healing and sore muscle relief, and to enhance skin absorption of therapeutic substances through heating of the substance and of the skin. The porous nature of the heating element 20 can hold various substances including various active pharmaceutical substances to enhance the healing, such as methyl salicylate. The heating element 20 can also be coated with any scent or fragrances to provide aromatherapy at the same time. Further, the heating element 20 of the present disclosure can be used as a disposable patient warmer to prevent hypothermia during a surgery or as a warming blanket for infants. The disposable nature of the heating element 20 allows for easier cleanup without transmission of substances between patients.

For scent-release applications, the heating element 20 can be partially or fully coated with scented wax, gel, liquid, or other scented, temperature-responsive material that can be released when the heating element 20 is heated. Controlled heating can be used to release single and separate scents at particular times, or to release combinations of scents. Such scent release applications include aromatherapy, home fragrances, insect repellent, layered timed release, and other suitable applications. For example, a heating article 10 can be designed to heat to 115 degrees Fahrenheit to release applied scents that melt, vaporize, or sublimate at or near that temperature, where the heating article 10 uses an in-wall or battery-powered power source. The heating article 10 can serve as a heater as well as a carrier substrate for scented material.

For cleaning applications, cleaning effectiveness can be amplified using a heated substrate to carry a suitable cleaning substance. For the example of a grease removal wipe, the heating element 20 can be heated to efficiently pick up more grease or oil on a surface by making the grease or oil less viscous and thus more receptive to being absorbed by the absorbent layer of the heating element 20. Such a cleaning tool can use less cleaning chemicals because of its increased effectiveness. Disposable mops, wipes, sponges, applicators, etc. can include a heating element 20 to boost their cleaning effectiveness.

Other applications are possible as well including providing heat in adverse or cold weather conditions to humans or animals. Heating articles 10 can be designed to fit arms, legs, torsos, necks, blankets and can even be used for animals such as horses, cattle, rabbits, various reptiles, dogs, and cats. These heating articles 10 can be used in extreme environments such as dry suits for divers, rescue suits for marine accidents, or other conditions of extreme cold such as automobile trouble in extreme cold environments. These heating articles 10 can also be used as a disposable heated bath towel for home, health care, or hotel uses. These heating elements 20 can be used for disposable heating liners for coats, ski suits, or other clothing. Additionally, these heating articles 10 can be used for warming common items such as beverage containers. A user can couple a semi-durable or reusable power source 50 to any of these aspects and use the product.

The heating article 10 is cost effective and can be tailored to the heating requirements of a particular application. Cost indicates that the heating element material is disposable per use, but the material is inherently durable enough, or could be manufactured as described above to be more durable, to allow for semi-durable or durable heating applications. The form factor of the heating element 20 allows for very specific tailoring of the heating characteristics. Process modifications to the conductive fiber content, basis weight, or size/shape of the heating element material can allow for flexibility of the heating element design. This variability allows the use of conductive paper for its resistive heating property in several applications. In addition, the heating element material itself is flexible and can conform to a user's body in an intimate and/or ergonomic manner.

Constructing the heating element 20 using the disclosed technology of a conductive web provides many advantages over current commercially available products that use exothermic chemical reactions. The portable heating device of the present disclosure allows disposable heating elements 20 to be made inexpensively compared to chemically-activated products. In addition, adjustable automatic controls allow the heating article 10 to regulate the amount of heat produced. Further, a power source 50 in the form of a battery 54 can be rechargeable or replaceable. Reflective material on the side opposite to the body increases thermal efficiency. Finally, the use of a fuse link can protect the wearer from overheating.

Experiment 1

In experimental development, 2"×4" sheets of conductive paper were prepared, including two strips (each 4 mm wide and running the entire width of the sheet) of silver printed ink on the paper at two opposite ends. Each sample was connected to a power supply by connecting the two silver ink strips to separate leads from the power supply. The samples were allowed to heat up (power on) for 5 minutes and cool down (power off) for 5 minutes. An infrared camera was used to capture the temperature of the paper at 4 frames per second. An average temperature over the entire surface area of the paper at each frame was calculated; a temperature curve as a function of time was created. Maximum temperature was calculated from an average temperature of the plateau region of the temperature curve. Maximum temperatures at a given power/area input and a given conductive fiber loading are shown in Table 1.

Experiment 2

An 8"×12" sheet of conductive paper at about 40 gsm and 35% by weight carbon fiber was prepared including two strips (each 0.5" wide and running the entire length of the sheet) of aluminum foil attached to the paper at two opposite ends. The sample was allowed to produce heat using a power supply by connecting to the two aluminum strips to separate leads from the power supply. At approximately 28 V and approximately 2 A, the sheet was heated in excess of 140 degrees Celsius. No evidence of char was observed.

Experiment 3

A scent release sample was made by coating 2 grams shea butter wax on a 2"×3" sheet of conductive paper. After connecting the paper to a power supply and allowing the paper to heat to 114 degrees Fahrenheit, a shea butter scent was observed in the air.

TABLE 1

| % Carbon Fiber in Conductive Paper | Voltage | Current | Power (W) | Power (W/m^2) | Max Temp. (Celsius) | Sample size (sq.m) |
|---|---|---|---|---|---|---|
| 30% carbon fiber | 5.565 | 0.097 | 0.538 | 112.613 | 29.82 | 0.004774 |
| 30% carbon fiber | 7.513 | 0.131 | 0.981 | 205.490 | 33.69 | 0.004774 |
| 30% carbon fiber | 10.639 | 0.186 | 1.974 | 413.577 | 43.43 | 0.004774 |
| 30% carbon fiber | 15.096 | 0.266 | 4.009 | 839.829 | 60.05 | 0.004774 |

TABLE 1-continued

| % Carbon Fiber in Conductive Paper | Voltage | Current | Power (W) | Power (W/m^2) | Max Temp. (Celsius) | Sample size (sq.m) |
|---|---|---|---|---|---|---|
| 30% carbon fiber | 21.342 | 0.491 | 10.479 | 2194.914 | 118.77 | 0.004774 |
| 10% carbon fiber | 6.069 | 0.087 | 0.529 | 110.710 | 28.86 | 0.004774 |
| 10% carbon fiber | 8.364 | 0.120 | 1.006 | 210.704 | 33.93 | 0.004774 |
| 10% carbon fiber | 11.848 | 0.171 | 2.026 | 424.392 | 43.94 | 0.004774 |
| 10% carbon fiber | 16.782 | 0.244 | 4.096 | 857.909 | 61.36 | 0.004774 |

These and other modifications and variations to the present disclosure may be practiced by those of ordinary skill in the art, without departing from the spirit and scope of the present disclosure, which is more particularly set forth in the appended claims. In addition, it should be understood that aspects of the various aspects of the present disclosure may be interchanged either in whole or in part. Furthermore, those of ordinary skill in the art will appreciate that the foregoing description is by way of example only, and is not intended to limit the disclosure so further described in such appended claims.

What is claimed:

1. A heating article comprising:

a heating element including a first layer of nonwoven fibers mixed with conductive fibers, wherein the layer is divided to include a conductive region and a nonconductive region, wherein the conductive region extends in a co-extensive and co-planar pattern in a majority of the layer, and wherein the conductive region has first and second ends; and a power source removably coupled to the first and second ends.

2. The heating article of claim 1, wherein at least a portion of the nonconductive region is formed by bonding.

3. The heating article of claim 1, wherein the first layer is absorbent.

4. The heating article of claim 1, wherein the nonwoven fibers include polymeric fibers.

5. The heating article of claim 1, wherein the heating element is disposable.

6. The heating article of claim 1, wherein the power source is rechargeable.

7. The heating article of claim 1, wherein the power source is durable.

8. The heating article of claim 1, wherein the power source is labeled for properly-oriented coupling to the first layer.

9. The heating article of claim 1, wherein the power source is coupled to the first layer with conductive hook material.

10. The heating article of claim 1, the heating element further comprising a second layer superposed with the first layer, wherein the second layer includes nonwoven fibers mixed with non-metallic conductive fibers, wherein the second layer is divided to include a conductive region and a nonconductive region.

11. The heating article of claim 10, wherein the first and second layers are separated by an insulating layer.

12. The heating article of claim 11, wherein the insulating layer is electrically insulating.

13. The heating article of claim 11, wherein the insulating layer is thermally insulating.

14. The heating article of claim 1, the heating element further comprising a water-resistant layer superposed with the first layer.

15. The heating article of claim 1, the heating element further comprising an absorbent layer superposed with the first layer.

16. The heating article of claim 1, the heating element further comprising a protective layer superposed with the first layer.

17. The heating article of claim 1, the heating element further comprising a heat-reflective layer superposed with the first layer.

18. The heating article of claim 1, further comprising a scent substance adapted to release a scent when heated.

19. The heating article of claim 1, wherein the conductive fibers are non-metallic.

20. A heating article comprising:

a heating element including a first layer of nonwoven fibers mixed with non-metallic conductive fibers, wherein the layer is divided to include a conductive region and a nonconductive region, wherein the conductive region extends in a co-extensive and co-planar pattern in a majority of the layer, and wherein the conductive region has first and second ends, and a second layer superposed with the first layer, wherein the second layer is substantially free of non-metallic conductive fibers; and a power source removably coupled to the first and second ends.

* * * * *